United States Patent [19]

Nagata et al.

[11] 4,396,694
[45] Aug. 2, 1983

[54] ORGANIC ELECTROPHOTOGRAPHIC SENSITIVE MATERIALS

[75] Inventors: Masayoshi Nagata; Seiji Horie; Junji Nakano; Hideo Sato, all of Asaka, Japan

[73] Assignee: Fuji Photo Film Co., Ltd., Kanagawa, Japan

[21] Appl. No.: 331,746

[22] Filed: Dec. 17, 1981

[30] Foreign Application Priority Data

Dec. 19, 1980 [JP] Japan .................. 55-180148

[51] Int. Cl.$^3$ .................. G03G 5/05
[52] U.S. Cl. .................. 430/58; 430/70; 430/71; 430/76; 430/74; 430/59
[58] Field of Search .................. 430/74, 58, 59

[56] References Cited

U.S. PATENT DOCUMENTS 4,150,987  4/1979  Anderson et al. .................. 430/58
4,278,747  7/1981  Murayama et al. .................. 430/82
4,297,426  10/1981  Saki et al. .................. 430/59
4,338,388  7/1982  Sakai et al. .................. 430/58

FOREIGN PATENT DOCUMENTS 930988  7/1958  United Kingdom .................. 430/70

Primary Examiner—John D. Welsh
Attorney, Agent, or Firm—Sughrue, Mion, Zinn, Macpeak, and Seas

[57] ABSTRACT

An electrophotographic sensitive material is described comprising an electrophotographic sensitive layer containing a compound represented by the formula (1)

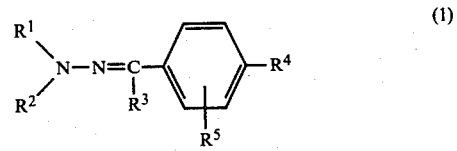

(1)

wherein $R^1$ and $R^2$ each represents an unsubstituted or substituted straight chain or branched chain alkyl group having from 1 to 12 carbon atoms, an unsubstituted or substituted straight chain or branched chain aralkyl group having from 7 to 20 carbon atoms or an aryl group consisting of a monovalent group consisting of an unsubstituted or substituted monocyclic aromatic hydrocarbon or polycyclic aromatic hydrocarbon having from 2 to 4 nuclei from which a hydrogen atom is removed; $R^3$ represents an unsubstituted or substituted straight chain or branched chain alkyl group having from 1 to 12 carbon atoms, an unsubstituted or substituted aralkyl group having from 7 to 20 carbon atoms or an unsubstituted or substituted aryl group; and $R^4$ and $R^5$ each represents an unsubstituted or substituted straight chain or branched chain alkyl group having from 1 to 12 carbon atoms, an unsubstituted or substituted nitrogen-containing heterocyclic compound from which a hydrogen atom is removed, a halogen atom, an alkoxy group, an aryloxy group, a dialkylamino group, or a hydrogen atom.

9 Claims, No Drawings

ORGANIC ELECTROPHOTOGRAPHIC SENSITIVE MATERIALS

FIELD OF THE INVENTION

The present invention relates to electrophotographic sensitive materials, and, more particularly, to electrophotographic sensitive materials having a layer containing a novel electric charge transport material.

BACKGROUND OF THE INVENTION

The photoconductive process in electrophotographic sensitive materials consists of (1) a step of generating electric charges by exposure and (2) a step of transporting the electric charges.

An example of carrying out steps (1) and (2) by means of a single substance includes a selenium electrophotographic sensitive plate, which is well known. On the other hand, an example of carrying out steps (1) and (2) by means of different substances, respectively, involves using a combination of amorphous selenium and poly-N-vinylcarbazole, which has been well known. The process of carrying out steps (1) and (2) by means of different substances, respectively, has advantages such as that the choices of selecting materials used for the electrophotographic sensitive materials is expanded, by which electrophotographic properties, such as sensitivity and acceptant electric potential, etc., of the sensitive materials, are improved and that materials suitable for production of a coating film of the sensitive material can be selected from a broad range of possibilities.

Hitherto, inorganic substances such as selenium, cadmium sulfide, zinc oxide, etc. have been used as the photoconductive material in the electrophotographic sensitive material used in electrophotographic processes.

As has been disclosed in U.S. Pat. No. 2,297,691, by Carlson, in the electrophotographic process, a photoconductive material comprising a base coated with a substance which is insulator in the dark, electric resistance of which varies corresponding to exposure by imagewise exposure to light, is used. This photo-conductive material is generally electrically charged in the dark after being subjected to dark adaptation for a suitable period of time. The material is then imagewise exposed to light in the form of a radiation pattern, which has the effect of reducing surface electric charges corresponding to the relative energy of the radiation pattern. The surface electric charges or electrostatic latent images remaining on the surface of the photoconductive layer (photosensitive layer) are then brought into contact with a suitable electroscopic indication material, namely, a toner, to form visible images. The toner is allowed to adhere to the surface of the sensitive layer corresponding to the electric charge pattern, whether the toner is contained in an insulating liquid or in a dry carrier. The indication material adhered on the surface can be fixed by known means such as by heat, pressure or a vapor of a solvent. Further, the electrostatic latent images can be transcribed onto a second base (for example, paper, film, etc.). Likewise, it is possible to develop the electrostatic latent images transcribed on the second base.

Basic characteristics required for the electrophotographic sensitive materials in such an electrophotographic process include the following: (1) the sensitive material can be electrically charged in the dark so as to have a suitable electric potential, (2) the degree of disappearance of electric charges is small in the dark, and (3) the electric charges can be rapidly dispersed by light exposure.

The above described inorganic substances used hitherto have various drawbacks at the same time they have a lot of advantages. For example, selenium, which is widely used at the present time, sufficiently satisfies the above described requirements (1) through (3). However, it has drawbacks in that the cost of production is high because of the severe conditions required for production, in that it is difficult to form into a belt because of lack of elasticity, and that it is necessary to pay attention to handling because it is sensitive to heat and mechanical shock. Cadmium sulfide and zinc oxide have been used as a sensitive material by dispersing in a resin binder but they can not be repeatedly used, because they have mechanical drawbacks with respect to smoothness, hardness, tensile strength, antifriction properties, etc.

In recent years, various electrophotographic sensitive materials using organic substances have been proposed, in order to overcome the drawbacks of the inorganic substances, and some of them have been put to practical use. Examples include a sensitive material comprising poly-N-vinylcarbazole and 2,4,7-trinitrofluorene-9-one (U.S. Pat. No. 3,484,237), a sensitive material composed of poly-N-vinylcarbazole sensitized with a pyrilium dyestuff (Japanese Patent Publication No. 25658/73), a sensitive material comprising an organic pigment as a main component (Japanese Patent Application (OPI) No. 37543/72) and a sensitive material comprising an eutectic complex composed of a dye and a resin (Japanese Patent Application (OPI) No. 10735/72). Although these sensitive materials are believed to have a high practical value because of having excellent characteristics, the fact is that there is no organic substance which completely satisfies the above described requirements for the sensitive materials in the electrophotographic process.

As a result of carrying out studies on photoconductive substances, it has now been found that hydrazone compounds represented by the formula (I), as described hereinafter, effectively function as photoconductive substances for the electrophotographic sensitive materials, and excellent as charge transport materials.

Examples of using hydrazone compounds in electrophotographic sensitive materials have been described in U.S. Pat. No. 3,717,462 (corresponding to Japanese Patent Publication 8137/73), Japanese Patent Application (OPI) No. 59143/79 (corresponding to U.S. Pat. No. 4,150,987) and Japanese Patent Applications (OPI) No. 52063/80 and 52064/80, etc. All of these examples are condensed polynuclear compounds or N-alkylamino substituted compounds.

Electrophotographic sensitive materials having a photosensitive layer containing N-arylamino substituted compounds have already been found and proposed in Japanese Patent Application (OPI) No. 85495/80. In the sensitive materials, oxidation caused by ozone generating by corona discharging, which is a fatal fault in the sensitive materials of the prior art, stability to heat and light, and dark decay, etc. are remarkably improved and resulted in forming electrophotographic sensitive materials which have high sensitivity, low residual electric potential, residual electric potential causing generally fog, narrow variation of the residual electric potential and the sensitivity even when repeatedly using the materials and excellent durability. However, a continuing need exists for improved electrophotographic sensitive materials having excellent characteristics.

SUMMARY OF THE INVENTION

An object of the present invention is to provide electrophotographic sensitive materials having an electrophotographic sensitive layer containing a novel charge transport material.

Another object of the present invention is to provide electrophotographic sensitive materials having an electrophotographic sensitive layer having high sensitivity wherein the residual electric potential is low.

Another object of the present invention is to provide electrophotographic sensitive materials having a stabilized electrophotographic sensitive layer which is stable to oxidation caused by ozone generating by corona discharging, light and heat, and shows little dark decay of electric potential, wherein the residual electric potential and the sensitivity do not substantially change even when repeatedly using the materials.

A further object of the present invention is to provide electrophotographic sensitive materials, handling and disposal of which can be safely carried out, which have an electrophotographic sensitive layer containing a novel charge transport material which is nontoxic or has low toxicity and can be synthesized using nontoxic or low toxicity raw materials.

Further, another object of the present invention is to provide a stabilized charge transport layer having high film strength and excellent uniformity, which results in less deterioration by fatigue.

The present invention provides electrophotographic sensitive materials which comprise a electrophotographic sensitive layer containing a compound represented by formula (1)

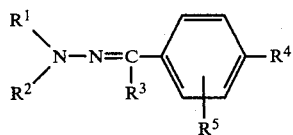

(1)

wherein $R^1$ and $R^2$ (which may be identical or different from each other) each represents an unsubstituted or substituted straight chain or branched chain alkyl group having from 1 to 12 carbon atoms, an unsubstituted or substituted straight chain or branched chain aralkyl group having from 7 to 20 carbon atoms, or an aryl group consisting of a monovalent group of an unsubstituted or substituted monocyclic aromatic hydrocarbon or polycyclic aromatic hydrocarbon having from 2 to 4 nuclei from which a hydrogen atom is removed (hereinafter also referred to more simply as the "aryl group"); and $R^1$ and $R^2$ (which may be identical or different from each other).

$R^3$ represents an unsubstituted or substituted straight chain or branched chain alkyl group having from 1 to 12 carbon atoms, an unsubstituted or substituted aralkyl group having from 7 to 20 carbon atoms or an unsubstituted or substituted aryl group;

$R^4$ and $R^5$, which may be identical or different from each other, each represents an unsubstituted or substituted straight chain or branched chain alkyl group having from 1 to 12 carbon atoms, an unsubstituted or substituted aralkyl group having from 7 to 20 carbon atoms, an unsubstituted or a substituted aryl group, an N-containing heterocyclic group a monovalent group consisting of an unsubstituted or substituted nitrogen containing heterocyclic compound from which a hydrogen atom is removed (hereinafter also referred to more simply as the "N-containing heterocyclic group"), a halogen atom, an alkoxy group, an aryloxy group, a dialkylamino group, or a hydrogen atom.

When $R^1$, $R^2$, $R^3$, $R^4$, or $R^5$ is an alkyl group, an aralkyl group, an aryl group, or a N-containing heterocyclic group which has substituents, the substituents can be selected from halogen atoms, alkoxy groups, aryloxy groups, dialkylamino groups and alkylthio groups; when $R^1$, $R^2$, $R^3$, $R^4$, $R^5$ is an aryl group or an N-containing heterocyclic group, the substituents can also be selected from alkyl groups; and when $R^1$, $R^2$, $R^3$, $R^4$ or $R^5$ is an alkyl group or an aryl group, the substituents can also be selected from N-containing heterocyclic groups in addition to the above described groups.

DETAILED DESCRIPTION OF THE INVENTION

Examples of $R^1$ and $R^2$ representing unsubstituted alkyl groups include a methyl group, an ethyl group, a propyl group, a butyl group, a pentyl group, a hexyl group, an octyl group, a nonyl group, a dodecyl group, an isopropyl group, an isobutyl group, an isopentyl group, a 4-methylpentyl group, a sec-butyl group, and a tert-butyl group. When $R^1$ and $R^2$ represent substituted alkyl groups, examples of the substituents thereof include halogen atoms such as chlorine, bromine, and fluorine, alkoxy groups such as a methoxy group, an ethoxy group, a propoxy group, a butoxy group, and a pentyloxy group, aryloxy groups such as an o-tolyloxy group, a m-tolyloxy group, a p-tolyloxy group, a 1-naphthyloxy group, and a 2-naphthyloxy group, dialkylamino groups such as a dimethylamino group, a diethylamino group, a dipropylamino group, a N-methyl-N-ethylamino group, a N-ethyl-N-propylamino group, and a N-methyl-N-propylamino group, alkylthio group, such as a methylthio group, an ethylthio group and a propylthio group, and N-containing heterocyclic groups such as a piperidino group, a 1-piperazinyl group, a morpholino group and a 1-pyrrolidyl group. Useful substituted alkyl groups include alkyl groups wherein at least one of the above described substituents is bonded to carbon atoms.

Examples of $R^1$ and $R^2$ representing unsubstituted aralkyl groups include a benzyl group, a phenetyl group, a 1-naphthylmethyl group, a 2-naphthylmethyl group, a 1-anthrylmethyl group, and a benzhydryl group. When $R^1$ and $R^2$ represent substituted aralkyl group, examples of the substituents thereof include the above described substituents. Useful substituted aralkyl groups include aralkyl groups wherein at least one of the above described substituents is bonded to carbon atoms.

Examples of $R^1$ and $R^2$ representing unsubstituted aryl groups include a phenyl group, a 1-naphthyl group, a 2-naphthyl group, an anthryl group, a pyrenyl group, an acenaphthenyl group and a fluorenyl group. When $R^1$ and $R^2$ represent substituted aryl groups, examples of the substituents thereof include the above described substituents and alkyl groups such as a methyl group, an ethyl group, a propyl group, a butyl group, a pentyl group, an isopropyl group, an isobutyl group, and an isopentyl group. Useful substituted aryl groups include aryl groups wherein at least one of the above described substituents is bonded to carbon atoms thereof.

Preferred combinations of $R^1$ and $R^2$ include combinations in which one of $R^1$ and $R^2$ is a phenyl group and the other is a methyl group, an ethyl group, a benzyl group, or a phenyl group.

When $R^3$, $R^4$, and $R^5$ represent unsubstituted or substituted alkyl groups, unsubstituted or substituted aralkyl groups, or unsubstituted or substituted aryl groups, examples thereof include the same groups as those described for $R^1$ and $R^2$. Examples of $R^4$ and $R^5$ representing unsubstituted N-containing heterocyclic groups include a piperidino group, a 1-piperazinyl group, a morpholino group and a 1-pyrrolidyl group. Examples of $R^4$ and $R^5$ representing substituted N-containing heterocyclic groups include a 2-methylpiperidino group, a 3-methylpiperidino group, 4-methylpiperidino group, a 2-ethylpiperidino group, 3-ethylpiperidino group, 4-ethylpiperidono group, a 2-propylpiperidino group, a 2-methyl-1-piperazinyl group, a 2-methylmorpholino group and a 2-methyl-1-pyrrolidyl group. Examples of $R^4$ and $R^5$ representing halogen atoms, alkoxy groups, aryloxy groups, or dialkylamino groups, include the same groups as those described above for $R^1$ and $R^2$.

Preferred examples of $R^3$ include a methyl group, an ethyl group, a phenyl group, a benzyl group, a p-(dimethylamino)phenyl group and a p-(diethylamino)phenyl group, and those of $R^4$ and $R^5$ include a hydrogen atom, a methyl group, an ethyl group, a methoxy group, an ethoxy group, a chlorine atom, a fluorine atom, a piperidino group, a morpholino group, a dimethylamino group, and a diethylamino group.

Examples of compounds represented by the formula (I) include the following compounds.

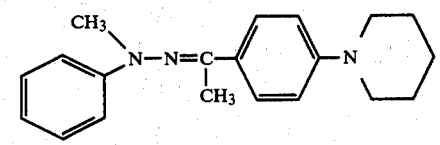
(1)

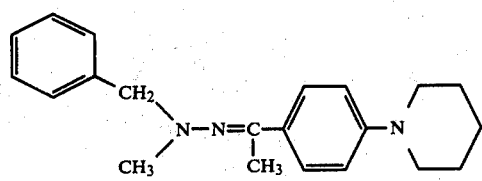
(2)

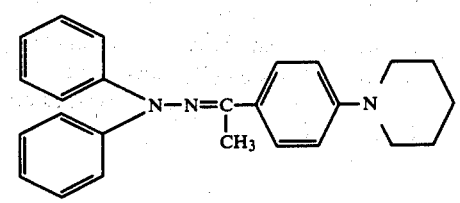
(3)

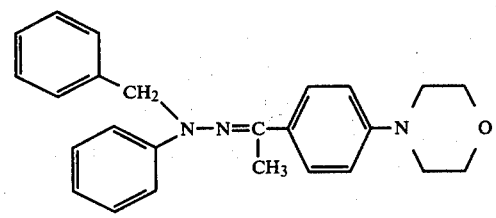
(4)

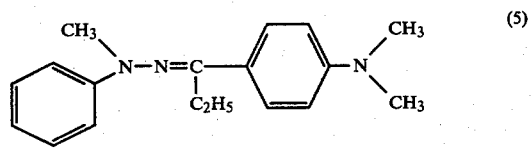
(5)

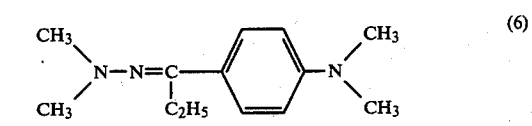
(6)

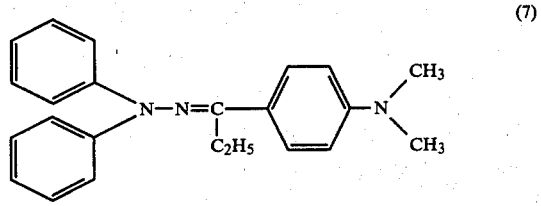
(7)

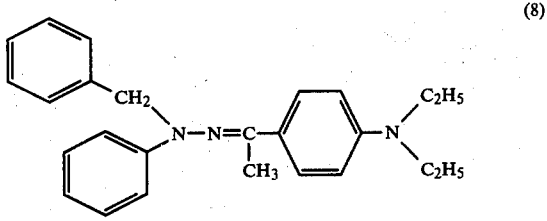
(8)

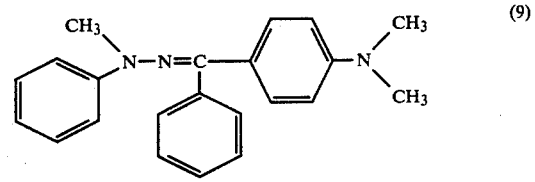
(9)

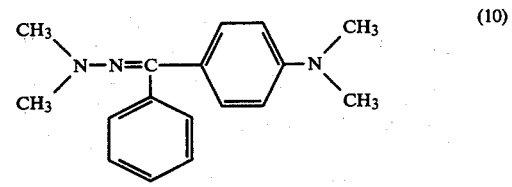
(10)

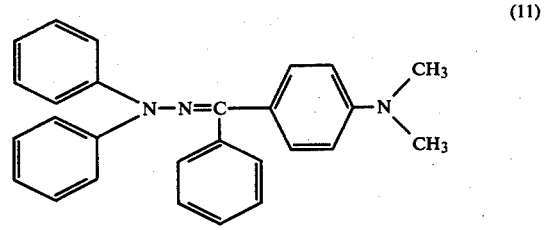
(11)

-continued
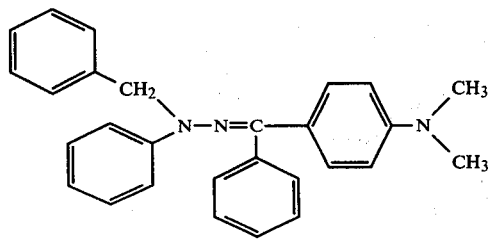 (12)
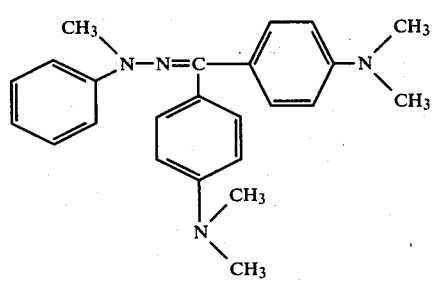 (13)
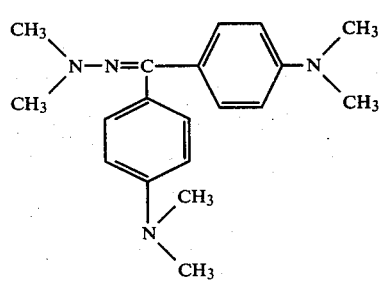 (14)
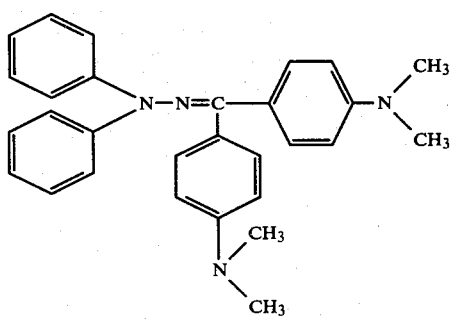 (15)
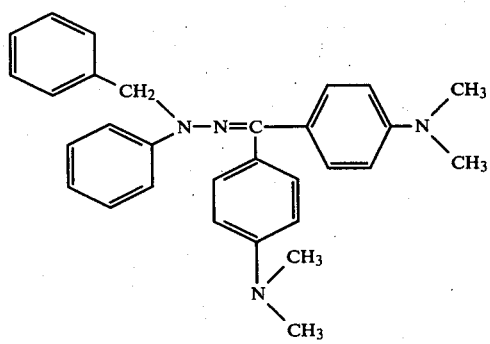 (16)
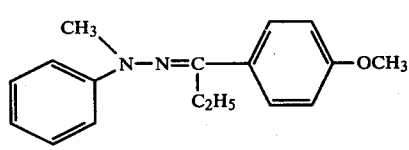 (17)
-continued
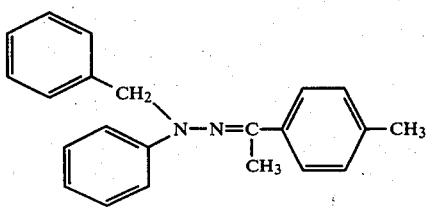 (18)
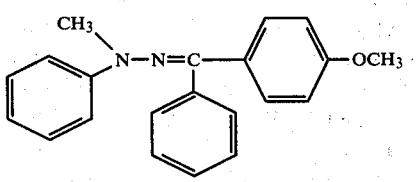 (19)
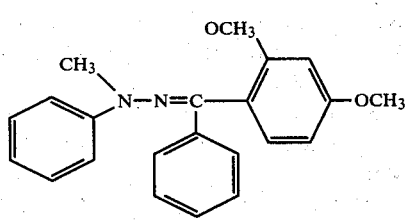 (20)
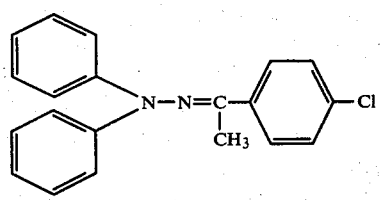 (21)
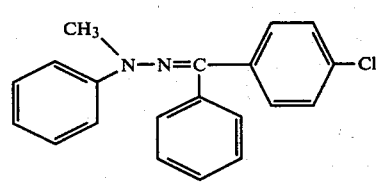 (22)
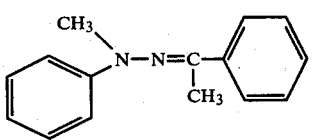 (23)
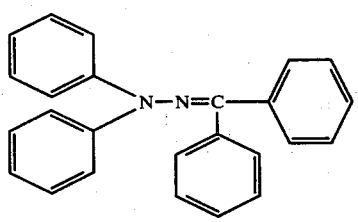 (24)
The compounds represented by the formula (1) can be synthesized by the reaction (2) below, which can be carried out according to the processes described in the documents listed below.

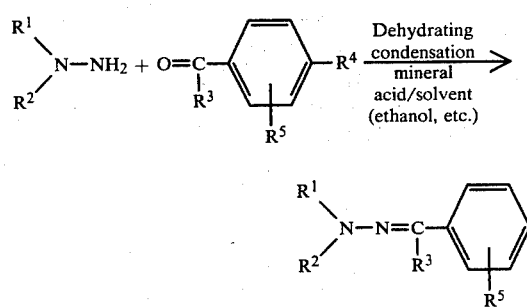

wherein $R^1$, $R^2$, $R^3$, $R^4$ and $R^5$ each have the same meaning as in the formula (1).

Documents:

R. H. Wiley, G. Irick "J. Org. Chem." Vol. 24, p. 1925 (1959); I. T. Millar, H. D. springall edit., "The Organic Chemistry of Nitrogen" (Oxford University Press, 1966) page 521 et seq.; G. Hilgetag, A. Martini edit., "Preparative Organic Chemistry" (John Wiley & Sons, Ltd., New York, 1968) page 508 et seq.; and S. Patai, edit., "The Chemistry of the Carbon-Nitrogen Double Bond" (Interscience Publishers, London, 1970) page 71 et seq.

Below, an example of synthesizing Compound (1) is described.

Example of synthesis:

15 m mols (millimoles) of 1-methyl-1-phenylhydrazine and 15 m mols of p-piperidinoacetophenone were dissolved in 50 ml of ethanol. After adding a few drops of concentrated hydrochloric acid, the solution was refluxed for 5 hours. The reacting solution was condensed, and it was made weakly alkaline by adding a saturated sodium carbonate aqueous solution to obtain a yellowish brown precipitate. After the precipitate was separated by filtration and dried, it was recrystallized from a mixed solvent of n-hexane/ethanol (1:1 by volume), by which 2.5 g of the Compound (1) was obtained. Melting point: 107°–108° C.

Yield: 55%.

By using the compounds represented by the formula (1) as a charge transport material, the film-forming property, the durability, the charging characteristics, and the residual electric potential characteristics of the electrophotographic sensitive layer are improved. Furthermore, since the compounds represented by formula (1) have excellent compatibility with various polymeric binders, the electrophotographic sensitive layer does not become cloudy or opaque, even if a large amount of the charge transport material is added. Consequently, since the polymeric binder to be used can be selected from a large number, and the range of the relative amount thereof is large, it is possible to produce electrophotographic sensitive materials having a suitable charge transport ability and a suitable film forming property for a variety of particular pruposes and uses.

Thus the compounds represented by formula (1) can be conveniently combined with suitable electric charge generating materials to produce effective electrophotographic sensitive materials.

Examples of the electric charge generating materials capable of use in the present invention include the following materials.

(1) Selenium and selenium alloys.
(2) Inorganic photoconductors such as CdS, CdSe, CdSSe, ZnO, ZnS, etc.
(3) Phthalocyanine pigments such as metal phthalocyanine or metal-free phthalocyanine, etc.
(4) Azo dyes such as monoazo dyes or diazo dyes, etc.
(5) Perylene pigments such as perylenic acid anhydride, perylenic acid imide, etc.
(6) Indigoid dyes.
(7) Quinacridone dyes.
(8) Polycyclic quinones such as anthraquinones, pyrenequinones, anthanthrones, flavanthrones, etc.
(9) Bisbenzimidazole pigments.
(10) Cyanine dyes.
(11) Squarylium derivatives.
(12) Indanthrone pigments.
(13) Xanthene pigments.
(14) Charge transport complexes composed of an electron donative substance such as poly-N-vinylcarbazole and an electron accepting substance such as trinitrofluorenone.
(15) Eutectic complexes composed of a pyrilium dye and a polycarbonate resin, etc.

The polymeric binder used together with the compounds represented by the formula (1) in the present invention is an electrically insulating film-forming high molecular weight polymer or copolymer which is hydrophobic and has a high dielectric constant. Examples of such high molecular weight polymers and copolymers include the following materials.

(1) Polystyrene resin.
(2) Polyvinyl chloride resin.
(3) Polyvinylidene chloride resin.
(4) Polyvinyl acetate resin.
(5) Acryl resin.
(6) Methacryl resin.
(7) Styrene-butadiene copolymer.
(8) Vinylidene chloride-acrylonitrile copolymer.
(9) Vinyl chloride-vinyl acetate copolymer.
(10) Silicone resin.
(11) Polyester resin.
(12) Polycarbonate resin.
(13) Styrene-alkyd resin.
(14) Silicone-alkyd resin.
(15) Phenol-formaldehyde resin.

These polymeric binders are used alone or as a mixture of two or more thereof. However, the polymeric binder capable of using in the present invention is not limited to the above described binders.

The sensitive materials of the present invention may be produced by dissolving or dispersing the electric charge generating material in the polymeric binder together with the charge transport material, and applying the resulting dispersion or solution to an electrically conductive base to provide a uniform layer. Further, the electrophotographic sensitive materials of the present invention have excellent electrophotographic characteristics when they have a two-layer construction wherein a charge generating layer comprising the electric charge generating material is provided on the electrically conductive layer, if necessary through an intermediate layer, and a charge transport layer comprising the charge transport material is provided on said charge generating layer so as to be adjacent to said layer. However, electrophotographic sensitive materials wherein fine particles of the electric charge generating material are dispersed in the charge transport layer provided on the electrically conductive base, again if necessary through an intermediate layer, can be effectively used in the present invention also.

Furthermore, in case of having a two layer construction consisting of the charge generating layer and the charge transport layer, the choice of which of them is to be the upper layer depends upon the selection of the charging polarity. Namely, in the case of charging negatively, more advantageous characteristics are obtained when the upper layer is the charge transport layer.

In the present invention, it is advantageous that the upper layer is the charge transport layer, because the compounds represented by the formula (1) exhibit positive charge transport predominance.

When the electrophotographic sensitive materials of the present invention are produced so as to have a two layer construction comprising a charge generating layer and a charge transport layer, the charge generating layer can be provided on an electrically conductive base immediately or, if desired, through an intermediate layer, such as a subbing layer, a barrier layer, etc., (1) by vacuum evaporation, (2) by applying a solution of an electric charge generating material in a suitable solvent, or (3) by applying a dispersion which is produced by milling an electric charge generating material in a dispersion medium by a ball mill or a homomixer, etc. and, if desired, by mixing with a polymeric binder. The polymeric binder used in this case may be the same material as that used for the charge transport layer.

The thickness of the charge generating layer composing the sensitive materials of the present invention is not particularly critical. However, it is preferred to provide it so as to have a thickness of from 0.05 $\mu$m to 5 $\mu$m and preferably from 0.1 $\mu$m to 3 $\mu$m. The thickness of the charge transport layer is not also particularly critical, but is preferably 5 $\mu$m to 30 $\mu$m.

In the present invention, the compounds of the present invention are used together with the polymeric binder.

In the case of using the charge generating material and the charge transport material in the same layer, it is preferred that the polymeric binder is used in an amount of from 0.8 to 4 parts by weight and the charge generating material is used in an amount of from 0.1 to 2 parts by weight, per 1 part by weight of compound according to formula (1).

In case of a two layer construction comprising the charge generating layer and the charge transport layer, it is preferred that the polymeric binder is used in an amount of from 0.8 to 4 parts by weight per 1 part by weight of the compound according to formula (1) in the charge transport layer, and the charge generating layer is produced by vacuum evaporation to have a thickness above described or by a dispersion or solution system. In the charge generating layer by the dispersion system, it is preferred that the polymeric binder be used in an amount of 10 parts by weight or less per 1 part by weight of the charge generating material.

In the case of having one layer construction of the present sensitive material, the thickness of the sensitive layer is not particularly critical, but is preferably from 3 $\mu$m to 50 $\mu$m, more preferably 5 $\mu$m to 20 $\mu$m.

As the electrically conductive base composing the sensitive materials of the present invention, various suitable material may be used, examples of which include electrically conductive paper and plastic bases prepared by applying an electrically conductive compound or a metal thin layer to a surface thereof, metal plates which are, if desired, plated or vacuum evaporated with, palladium, aluminium, etc., aluminum plates, etc.

Further, as materials for composing the intermediate layer provided as occasion demands, it is possible to use polymeric compounds, such as casein, gelatine, starch, polyvinyl alcohol, polyvinyl acetate, ethyl cellulose, or carboxymethyl cellulose, etc. or metal oxides, such as aluminium oxide, in addition to the above described polymeric binders.

The present invention is illustrated below in greater detail by examples. However, the present invention is not limited to these examples. In the following examples, all parts are by weight.

EXAMPLE 1

A selenium layer having a thickness of 0.4 $\mu$m was provided on a surface of a finely sanded aluminum plate having a thickness of 0.3 mm by vacuum evaporation to form a charge generating layer. After a solution prepared by dissolving 4.6 parts of the Compound (1) and 5.4 parts of polycarbonate of bisphenol A in 78 parts of 1,2-dichloromethane was applied to the resulting layer by means of a wire wound rod, it was dried to form a charge transport layer having a thickness of 8 $\mu$m. Thus, an electrophotographic sensitive material having an electrophotographic sensitive layer composed of two layers was produced.

This sensitive material was negatively electrically charged by corona discharging at $-5$ KV using a testing machine for electrostatic copying paper (SP-428, produced by Kawaguchi Electric Co.) and it was then exposed to light using a tungsten lamp having a color temperature of 3000° K. so that the surface had 4.5 luxes. When the half decay exposure amount $E_{50}$ (Lux-sec) was measured by determining a period of time necessary to reduce the surface electric potential to half of the initial surface electric potential, it was 4 Lux-sec.

EXAMPLE 2

An electrophotographic sensitive material having an electrophotographic sensitive layer composed of two layers was produced by the same procedure as in Example 1, except that 4.2 parts of Compound (5) was used instead of Compound (1). When the characteristic of electric potential reduction by negative charging was measured in the same manner as in Example 1, the half decay exposure amount $E_{50}$ was 4.05 Lux-sec. When the two steps of charging and exposure were repeated 3000 times, the value of $E_{50}$ remained substantially constant.

EXAMPLE 3-6

Electrophotographic sensitive materials were produced by the same procedure as in Example 1, except that 5.6 parts of Compound (8), 5 parts of Compound (9), 5.6 parts of Compound (13) and 4.0 parts of Compound (17) were used, respectively, instead of Compound (1), and the half decay exposure by negatively charging was measured.

| Example | Compound | $E_{50}$ (Lux-sec) |
| --- | --- | --- |
| 3 | (8) | 7 |
| 4 | (9) | 5.1 |
| 5 | (13) | 6.5 |
| 6 | (17) | 8 |

EXAMPLE 7

5 parts of β-copper phthalocyanine were added to 660 parts of dichloromethane. After being dispersed by ultrasonic dispersion, 40 parts of polycarbonate of bisphenol A and 40 parts of Compound (1) were added to the resulting dispersion and dissolved therein to prepare a coating solution.

This coating solution was applied to an electrically conductive transparent base (a vacuum evaporation layer of indium oxide was provided on the surface of a polyethylene terephthalate film having a thickness of 100 μm; surface electric resistance: $10^3$) by means of a wire wound rod and dried to produce an electrophotographic sensitive material having an electrophotographic sensitive layer having a thickness of 9.5 μm.

After this sensitive material was positively electrically charged by corona discharging at +5 KV, the half decay exposure amount was measured. $E_{50}$ was 27 Lux-sec.

EXAMPLE 8-11

Electrophotographic sensitive materials were produced by the same procedure as in Example 7, except that Compounds (2), (7), (12) and (16) were used, respectively, instead of Compound (1), and the half decay exposure was measured by the same manner as in Example 7.

| Example | Compound | $E_{50}$ (Lux-sec) |
|---------|----------|--------------------|
| 8 | (2) | 30 |
| 9 | (7) | 25 |
| 10 | (12) | 30 |
| 11 | (16) | 32 |

EXAMPLE 12

2 parts of Chloro Dian Blue represented by the structural formula below and 2 parts of polycarbonate of bisphenol A were added to 260 parts of dichloromethane, and the mixture was milled in a ball mill to prepare a coating solution. This coating solution was applied to an electrically conductive transparent base (a vacuum evaporation layer was provided on a surface of a polyethylene terephthalate film having 100 μm; surface resistance: $10^3 \Omega$) by means of a wire wound rod, and it was dried to form a charge generating layer having a thickness of 1 μm.

To the charge generating layer, a solution prepared by dissolving 2 parts of Compound (1) and 4 parts of polycarbonate of bisphenol A in 60 parts of dichloromethane was applied by means of a wire wound rod and dried to form a charge transport layer having a thickness of about 8 μm.

When the half decay exposure amount by negative charging was measured in the same manner as in Example 1 using the resulting electrophotographic sensitive material having a sensitive layer composed of two layers, $E_{50}$ was 8 Lux-sec.

Structual formula of Chloro Dian Blue:

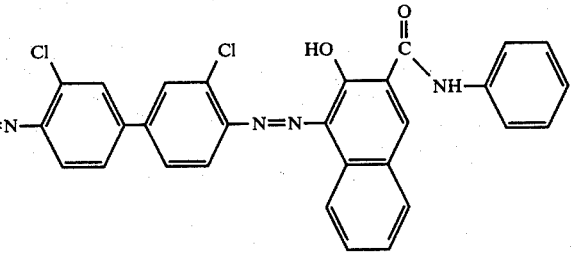

While the invention has been described in detail and with reference to specific embodiments thereof, it will be apparent to one skilled in the art that various changes and modifications can be made therein without departing from the spirit and scope thereof.

What is claimed is:

1. An electrophotographic sensitive material comprising an electrophotographic sensitive layer containing a compound represented by formula (1)

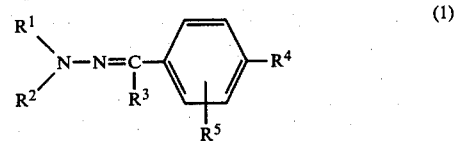

wherein $R^1$ and $R^2$ each represents an unsubstituted or substituted straight chain or branched chain alkyl group having from 1 to 12 carbon atoms, an unsubstituted or substituted straight chain or branched chain aralkyl group having from 7 to 20 carbon atoms, or an aryl group consisting of a monovalent group consisting of an unsbustituted or substituted monocyclic aromatic hydrocarbon or a polycyclic aromatic hydrocarbon having from 2 to 4 nuclei from which a hydrogen atom is removed; $R^3$ represents an unsubstituted or substituted straight chain or branched chain alkyl group having from 1 to 12 carbon atoms, an unsubstituted or substituted aralkyl group having from 7 to 20 carbon atoms or an unsubstituted aryl group; and $R^4$ and $R^5$ each represents an unsubstituted or substituted straight chain or branched chain alkyl group having from 1 to 12 carbon atoms, an unsubstituted or substituted aralkyl group having from 7 to 20 carbon atoms, an N-containing heterocyclic group consisting of a monovalent group consisting of an unsubstituted or substituted nitrogen-containing heterocyclic compound from which a hydrogen atom is removed, a halogen atom, an alkoxy group, an aryloxy group, a dialkylamino group, or a hydrogen atom;

wherein the electrophotographic sensitive layer is composed of a single layer containing a charge transport material represented by formula (1) and a charge generating material.

2. An electrophotographic sensitive material as in claim 1, wherein:

the substituents can be selected from halogen atoms, alkoxy groups, aryloxy groups, dialkylamino groups or alkylthio groups when $R^1$, $R^2$, $R^3$, $R^4$, or $R^5$ represents an alkyl group, aralkyl group, aryl group, or N-containing heterocyclic group which has substituents;

the substituents can also be selected from alkyl groups when $R^1$, $R^2$, $R^3$, $R^4$, or $R^5$ represents an aryl group or an N-containing heterocyclic group; and the substituents can also be selected from N-containing heterocyclic groups when $R^1$, $R^2$, $R^3$, $R^4$ or $R^5$ represents an alkyl group or an aryl group.

3. An electrophotographic sensitive material comprising an electrophotographic sensitive layer containing a compound represented by formula (1)

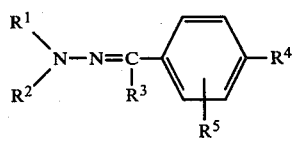

(1)

wherein $R^1$ and $R^2$ each represents an unsubstituted or substituted straight chain or branched chain alkyl group having from 1 to 12 carbon atoms, an unsubstituted or substituted straight chain or branched chain aralkyl group having from 7 to 20 carbon atoms, or an aryl group consisting of a monovalent group consisting of an unsubstituted or substituted monocyclic aromatic hydrocabon or a polycyclic aromatic hydrocarbon having from 2 to 4 nuclei from which a hydrogen atom is removed; $R^3$ represents an unsubstituted or substituted straight chain or branched chain alkyl group having from 1 to 12 carbon atoms, an unsubstituted or substituted aralkyl group having from 7 to 20 carbon atoms or an unsubstituted aryl group; and $R^4$ and $R^5$ each represents an unsubstituted or substituted straight chain or branched chain alkyl group having from 1 to 12 carbon atoms, an unsubstituted or substituted aralkyl group having from 7 to 20 carbon atoms, an N-containing heterocyclic group consisting of a monovalent group consisting of an unsubstituted or substituted nitrogen-containing heterocyclic compound from which a hydrogen atom is removed, a halogen atom, an alkoxy group, an aryloxy group, a dialkylamino group, or a hydrogen atom;

wherein the electrophotographic sensitive layer is composed of two layers comprising a charge generating layer, and a charge transport layer containing a compound represented by formula (1).

4. An electrophotographic sensitive material as in claim 3, wherein the charge generating layer has a thickness of from 0.05 μm to 5 μm.

5. An electrophotographic sensitive material as in claim 3, wherein the charge transport layer has a thickness of from 5 μm to 30 μm.

6. An electrophotographic sensitive material as in claim 3, wherein the charge transparent layer comprises from 0.8 to 4 parts by weight of polymeric binder per one part by weight of compound according to formula (1).

7. An electrophotographic sensitive material as in claim 3, wherein the charge generating layer comprises 10 parts by weight or less of polymeric binder per one part by weight of compound according to formula (1).

8. An electrophotographic sensitive material as in claim 3, wherein the charge generating layer is produced by vacuum evaporation of the charge generating material.

9. An electrophotographic sensitive material as in claim 3, wherein:

the substituents can be selected from halogen atoms, alkoxy groups, aryloxy groups, dialkylamino groups or alkylthio groups when $R^1$, $R^2$, $R^3$, $R^4$, or $R^5$ represents an alkyl group, aralkyl group, aryl group, or N-containing heterocyclic group which has substituents;

the substituents can also be selected from alkyl groups when $R^1$, $R^2$, $R^3$, $R^4$, or $R^5$ represents an aryl group or an N-containing heterocyclic group; and the substituents can also be selected from N-containing heterocyclic groups when $R^1$, $R^2$, $R^3$, $R^4$ or $R^5$ represents an alkyl group or an aryl group.

* * * * *